US006596879B2

(12) United States Patent
Bosch et al.

(10) Patent No.: US 6,596,879 B2
(45) Date of Patent: Jul. 22, 2003

(54) PROCESS FOR THE SYNTHESIS OF 1,3-DIOLS

(75) Inventors: Robert Lee Bosch, Allendale, MI (US); Richard Joseph McCabe, Holland, MI (US); Thomas Norman Nanninga, Holland, MI (US); Robert Joseph Stahl, Holland, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/166,990

(22) Filed: Jun. 11, 2002

(65) Prior Publication Data

US 2002/0161021 A1 Oct. 31, 2002

Related U.S. Application Data

(62) Division of application No. 09/581,798, filed as application No. PCT/US98/25493 on Dec. 2, 1998, now Pat. No. 6,433,213.
(60) Provisional application No. 60/068,193, filed on Dec. 19, 1997.

(51) Int. Cl.$^7$ ............................................. C07D 209/88
(52) U.S. Cl. ................. 548/441; 548/376.1; 548/377.1; 548/469
(58) Field of Search ............................ 548/250, 376.1, 548/377.1, 469

(56) References Cited

U.S. PATENT DOCUMENTS

| | | | | |
|---|---|---|---|---|
| 4,645,854 A | | 2/1987 | Verhoeven et al. | 560/60 |
| 4,897,490 A | * | 1/1990 | Sit et al. | 548/253 |
| 4,898,949 A | * | 2/1990 | Wright et al. | 548/253 |
| 4,970,313 A | | 11/1990 | Wess et al. | 544/335 |
| 5,155,251 A | | 10/1992 | Butler et al. | 558/442 |
| 5,273,995 A | * | 12/1993 | Roth | 514/422 |
| 5,298,627 A | * | 3/1994 | Butler et al. | 548/517 |
| 5,354,772 A | | 10/1994 | Kathawala | 514/414 |

FOREIGN PATENT DOCUMENTS

EP 0742209 A 11/1996

OTHER PUBLICATIONS

M. Sato et al., "Aldol Reaction of 4–Trimethylsiloxy–6–methylene–1,3–dioxines with Chiral Aldehydes: Enantioselective Synthesis of 1,3–Dioxin–4–ones Having a 2,3–Dihydroxylated Alkyl Group at the 6–Position," Tetrahedron Asymmetry, vol. 3, No. 9, 1992, pp. 1157–1160.

J.E. Lynch et al., "Synthesis of an HMG–CoA reductase inhibitor; a diastereoselective aldol approach," Tetrahedron Letters, vol. 28, No. 13, 1987, pp. 1385–1388.

M. Sletzinger et al., "A diastereospecific non–racemic synthesis of a novel beta–hydroxy–delta–lactone HMG–CoA reductase inhibitor," Tetrahedron Letters, vol. 26, No. 25, 1985, pp. 2951–2954.

K.–M. Chen et al., "1,3–Syn Diastereoselective Reduction of beta–hydroxyketones Utlizing Alkoxydialkylboranes," Tetrahedron Letters, vol. 28, No. 2, pp. 155–158.

K.–M. Chen et al., "A Novel Method for the In Situ Generation of Alkoxydialkylboranes and Their Use in the Selective Preparation of 1,3–Syn Diols," Chemistry Letters, 1987, pp. 1923–1926.

N. Narasaka et al., "Stereoselective Reduction of Beta–hydroxyketones to 1,3–Diols," Tetrahedron, vol. 40, No. 12, 1984, pp. 2233–2238.

P. Brower, "The Synthesis of (4R–cis)–1,1–Dimethylethyl 6–cyanomethyl–2,2–dimethyl–1,3–dioxane–4–acetate, a Key Intermediate for the Preparation of CI–981, a Highly Potent, Tissue Selective Inhibitor of HMG–CoA Reductase," Tetrahedron Letters, vol. 33, No. 17, 1992, pp. 2279–2282.

I. Paterson, "Towards the Synthesis of Swinholide A and Scytophycin C. A Highly Stereocontrolled Synthesis of (–)–Pre–Swinholide A.," Tetrahedron Letters, vol. 35, No. 20, 1994, pp. 3405–3408.

International Search Report (PCT/US98/25493).

Prasad, K., et al, "A Highly Stereoselective Route to the Four Stereoisomers of a Six–Carbon Synthon", Tetrahedron: Asymmetry, vol. 1, No. 5, 1990; pp 307–310.

* cited by examiner

*Primary Examiner*—D. Margaret Seaman
(74) *Attorney, Agent, or Firm*—Francis J. Tinney

(57) ABSTRACT

An improved process for the preparation of cis-1,3-diols is described where a beta hydroxy ketone is treated with a trialkylborane or dialkylalkoxyborane or a mixture of a trialkylborane and a dialkylalkoxyborane followed by recovery and reuse of the alkylborane species to convert additional beta hydroxy ketone to the cis-1,3-diol.

16 Claims, No Drawings

PROCESS FOR THE SYNTHESIS OF 1,3-DIOLS

This application is a divisional application of U.S. Ser. No. 09/581,798, filed Jun. 16, 2000, now U.S. Pat. No. 6,433,213 B1, which is a 371 of PCT/US98/25493, filed Dec. 2, 1998, which claims benefit of U.S. Provisional Application Ser. No. 60/068,193, filed Dec. 19, 1997.

BACKGROUND OF THE INVENTION

The present invention relates to a process for preparing cis-1,3-diols. More particularly, the present invention relates to the use and subsequent recovery and reuse of a trialkylborane or dialkylalkoxyborane or a mixture of a trialkylborane and a dialkylalkoxyborane in the reduction of a beta-hydroxy ketone to obtain a cis-1,3-diol. Additionally, the present invention relates to the use of a synergistic combination of a trialkylborane and a dialkylalkoxyborane in the reduction of a beta-hydroxy ketone to obtain a cis-1,3-diol.

The use of trialkylboranes or dialkylalkoxyboranes in the stereoselective reduction of 1,3-keto alcohols to the corresponding syn-1,3-diols has been widely described in the literature. This method has given high stereoselectivity without using extraordinarily difficult conditions (Brower P. L., Butler D. E., Deering C. F., Le T. V., Millar A., Nanninga T. N., and Roth B., *Tetrahedron Lett.*, 1992;33:2279; Narasaka K., and Pai F. C., *Tetrahedron*, 1984;40:2233; Chen K. M., Hardtmann G. E., Prasad K., Repic O., and Shapiro M. J., *Tetrahedron Lett.*, 1987;28:155; Chen K. M., Gunderson K. G., Hardtmann G. E., Prasad K., Repic O., and Shapiro M. J., *Chem. Lett.*, 1987:1923). There seems to be general acceptance of the formation of a borate ester from either the trialkyl or dialkylalkoxyboranes which is said to form a cyclic chelate (Narasaka K. and Pai F. C., *Tetrahedron*, 1984;40:2233; Chen K. M., Hardtmann G. E., Prasad K., Repic O., and Shapiro M. J., *Tetrahedron Lett.*, 1987;28:155; Chen K. M., Gunderson K. G., Hardtmann G. E., Prasad K., Repic O., and Shapiro M. J., *Chem. Lett.*, 1987:1923; see for example Paterson I., Cumming J. G., and Smith J. D., *Tetrahedron Lett.*, 1994;35:3405). Axial delivery of a hydride to the complex then leads predominately to the syn-product which can be hydrolyzed to the diol. The diols are valued as intermediates for the preparation of, for example, HMG-CoA reductase inhibitors which are useful hypolipidemic and hypocholesterolemic agents. This is a widely used method of preparation of such agents (U.S. Pat. Nos. 4,645,854, 5,354,772, 5,155,251, and 4,970,313).

Many procedures in the literature, describe the work-up of the reaction with hydrogen peroxide (U.S. Pat. No. 4,645,854 and 4,970,313). This results in the destruction of active alkylborane species. Some procedures describe the repeated distillation with methanol and an acid (U.S. Pat. No. 5,354,772 and 5,155,251). This also dilutes and eventually destroys the active alkylborane species. We have surprisingly and unexpectedly found that by performing the reduction and workup with a minimal amount of acid, and keeping the distillate streams separated, that the initial distillate can be recovered and reused to obtain very good selectivity in subsequent reductions.

Thus, the present process offers significant advantages over the prior art processes. For example, the cost of additional alkylborane is eliminated for each batch in which the distillate stream is recycled. Additionally, since alkylboranes are hazardous, they must be destroyed prior to being disposed. The present process minimizes this expensive and time-consuming procedure. Moreover, it is especially surprising that very good selectivity in the reductions is obtained using recovered alkylboranes.

Finally, we have also surprisingly and unexpectedly found that a combination of a trialkylborane and a dialkylalkoxyborane is synergistic in selectively reducing a beta-hydroxy ketone to obtain a cis-1,3-diol.

SUMMARY OF THE INVENTION

Accordingly, a first aspect of the present invention is a process for the preparation of a compound of Formula I

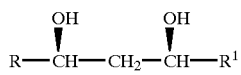

wherein R is alkyl,

NC—$CH_2$—,

PG—O—$CH_2$— wherein PG is a protecting group,

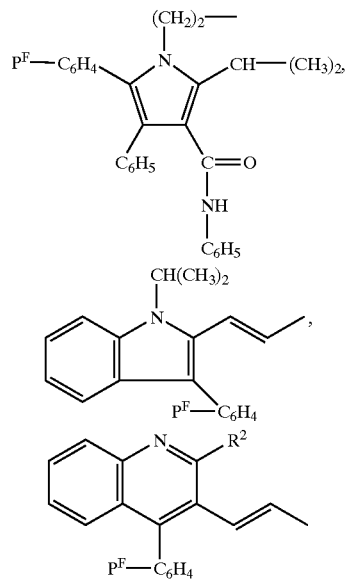

wherein $R^2$ is $(H_3C)_2CH$— or cyclopropyl,

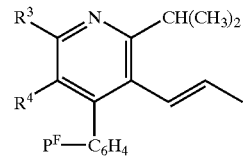

wherein $R^3$ is $C_6H_5$, $(H_3C)_2$—N— or $(H_3C)_2CH$— and $R^4$ is hydrogen, $H_3C$—O—$CH_2$—, $H_3C$—$CH_2$—$C(CH_3)_2$—$CO_2CH_2$—, or $H_3C$—$O_2C$—$CH_2$—CH(OH)—$CH_2$—CH(OH)—CH═CH—,

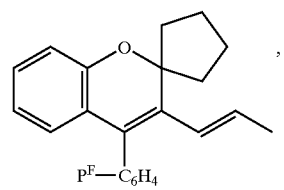

-continued

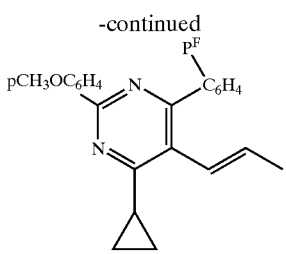

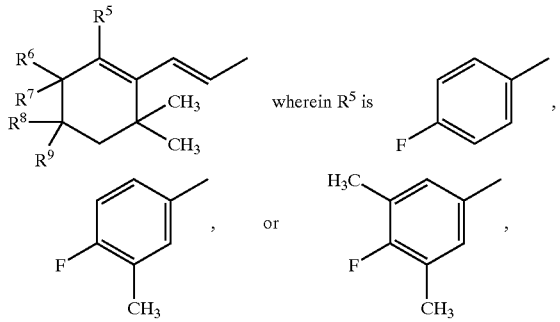

wherein $R^5$ is $R^6$ is hydrogen or $CH_3$, $R^7$ is hydrogen or $CH_3$, $R^8$ is hydrogen, OH, $CH_3$, or $H_5C_6$—NHCO—O—, and $R^9$ is hydrogen or $CH_3$,

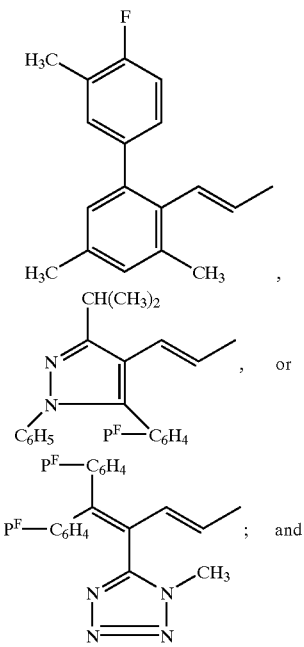

$R^1$ is alkyl, or —$CH_2$—$CO_2R^6$ wherein $R^6$ is alkyl;

which comprises:

Step (a) treating a compound of Formula II

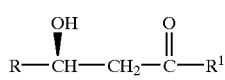

or a compound of Formula III

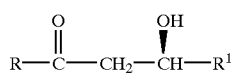

wherein R and $R^1$ are as defined above with a trialkylborane or dialkylalkoxyborane or a mixture of a trialkylborane and a dialkylalkoxyborane in a solvent;

Step (b) adding an alkali metal hydride at about −110° C. to about −50° C.;

Step (c) concentrating the reaction by distillation to afford a compound of Formula I and a distillate containing alkylborane species; and Step (d) treating additional compound of Formula II or III with the distillate from Step (c) containing recovered alkylborane species and repeating Steps (b) and (c) as desired to afford additional compound of Formula I.

A second aspect of the present invention is a process for the preparation of a compound of Formula I

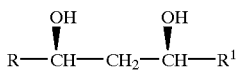

wherein R is alkyl,

NC—$CH_2$—,

PG—O—$CH_2$— wherein PG is a protecting group,

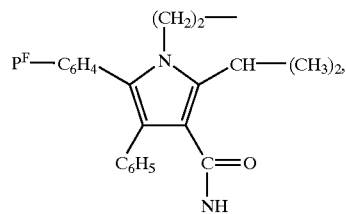

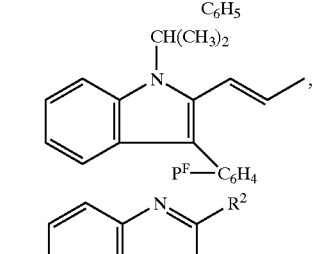

wherein $R^2$ is $(H_3C)_2CH$— or cyclopropyl,

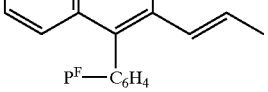

wherein $R^3$ is $C_6H_5$, $(H_3C)_2$—N— or $(H_3C)_2CH$— and $R^4$ is hydrogen, $H_3C$—O—$CH_2$—, $H_3C$—$CH_2$—$C(CH_3)_2$—$CO_2CH_2$—, or $H_3C$—$O_2C$—$CH_2$—$CH(OH)$—$CH_2$—

$CH(OH)$—$CH$=$CH$—,

-continued

[Structure: chromene-spirocyclopentane with p^F-C6H4 substituent]

[Structure: pyrimidine with pCH3OC6H4, p^F-C6H4, and cyclopropyl substituents]

[Structure: cyclohexene with R^5, R^6, R^7, R^8, R^9, two CH3 groups and propenyl]

wherein R^5 is

[p-tolyl with F structure], [3-methyl-4-fluorophenyl structure], or [3,5-dimethyl-4-fluorophenyl structure]

R^6 is hydrogen or CH3, R^7 is hydrogen or CH3,

R^8 is hydrogen, OH, CH3, or  H5C6—NHCO—O—, and

R^9 is hydrogen or CH3,

[Structure: biphenyl with F, two CH3 groups, and propenyl]

[Structure: pyrazole with CH(CH3)2, C6H5, p^F-C6H4, and propenyl] , or

[Structure: tetrazole with two p^F-C6H4 groups, CH3, and propenyl] ; and

R^1 is alkyl, or  —CH2—CO2R^6 wherein R^6 is alkyl;

which comprises:

Step (a) treating a compound of Formula II $$R-\underset{\underset{\text{OH}}{|}}{CH}-CH_2-\underset{\underset{\text{O}}{\|}}{C}-R^1 \qquad \text{II}$$

or a compound of Formula III $$R-\underset{\underset{\text{O}}{\|}}{C}-CH_2-\underset{\underset{\text{OH}}{|}}{CH}-R^1 \qquad \text{III}$$

wherein R and $R^1$ are as defined above with a synergistic combination of a trialkylborane and a dialkylalkoxyborane in a solvent; and Step (b) adding an alkali metal hydride at about −110° C. to about −50° C. to afford a compound of Formula I.

A third aspect of the present invention is a synergistic combination comprising a trialkylborane and a dialkylalkoxyborane.

DETAILED DESCRIPTION OF THE INVENTION

In this invention the term "alkyl" means a straight or branched hydrocarbon radical having from 1 to 10 carbon atoms and includes, for example, methyl, ethyl, n-propyl, isopropyl, n-butyl, secondary-butyl, isobutyl, tertiary butyl, n-pentyl, n-hexyl, n-heptyl, n-octyl, n-nonyl, n-decyl, and the like.

"PG" means a protecting group used for protecting an alcohol moiety such as, for example, benzyl and the like. Additional examples of protecting groups for an alcohol moiety are disclosed at Chapter 2 in Greene T. W., "Protective Groups in Organic Synthesis", John Wiley & Sons, Inc., 1981.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, and the like.

"Alkali metal hydride" includes, for example, sodium borohydride, zinc borohydride, lithium borohydride, lithium aluminum hydride, and the like.

"Alkylborane species" means a mono, di- or trialkylborane where the mono or dialkylborane is further substituted by hydrido or alkoxy as defined hereinafter or a dimeric alkylborane species.

"Alkoxy" means O-alkyl as defined above for alkyl.

As previously described, the compounds of Formula I are either useful as inhibitors of the enzyme 3-hydroxy-3-methylglutaryl-coenzyme A reductase (HMG CoA reductase) or are useful as intermediates to prepare HMG CoA reductase inhibitors.

Thus, the present process can be used to prepare various HMG CoA reductase inhibitors containing a cis-1,3-diol moiety. For example, atorvastatin disclosed and described in U.S. Pat. Nos. 4,681,893 and 5,273,995; fluvastatin disclosed and described in U.S. Pat. No. 5,354,772; bervastatin disclosed and described in U.S. Pat. No. 5,082,859; cerivastatin disclosed and described in U.S. Pat. No. 5,177,080; NK-LO4 disclosed and described in U.S. Pat. No. 5,011,930; dalvastatin disclosed and described in U.S. Pat. No. 4,863,957; glenvastatin disclosed and described in U.S. Pat. No.

4,925,852; erythro-7-[5-(2,2-dimethylbutyryloxymethyl)-4-(4-fluorophenyl)-2,6-diisopropylpyridin-3-yl]-3,5-dihydroxy-6(E)-heptenoic methyl ester disclosed and described in U.S. Pat. Nos. 5,006,530, 5,169,857, and 5,401,746; 7,7'-[2-(dimethylamino)-4-(4-fluorophenyl)-6-isopropylpyridine-3,5-diyl]bis [erythro-(E)-3,5-dihydroxy-6-heptenoic acid methyl ester disclosed and discribed in U.S. Pat. No. 5,145,857; 7-[6-cyclopropyl-4-(4-fluorophenyl)-2-(4-methoxyphenyl)pyrimidin-5-yl]-3,5-dihydroxy-6(E)-heptenoic acid sodium salt disclosed and described in U.S. Pat. No. 5,026,708; (E)-7-[4-(4-fluorophenyl)-2-isopropylquinolin-3-yl]-3,5-dihydroxy-6-heptenoic acid δ-lactone disclosed and described in U.S. Pat. Nos. 5,011,930, 5,102,888, and 5,185,328; trans-(E)-6-[2-[2-(4-fluoro-3-methylphenyl)-6,6-dimethyl-4-(N-phenyl-carbamoyloxy)-1-cyclohexenyl]vinyl]-4-hydroxytetrahydropyran-2-one disclosed and described in U.S. Pat. No. 5,001,144; erythro-(E)-7-[2-(4-fluoro-3-methylphenyl)-4,4,6,6-tetramethyl-1-cyclohexen-1-yl]-3,5-dihydroxy-6-heptenoic acid sodium salt disclosed and described in U.S. Pat. No. 4,863,957; (E)-trans-6-[2-[2-(4-fluoro-3,5-dimethylphenyl)-4-hydroxy-6,6-dimethyl-1-cyclohexenyl]vinyl]-4-hydroxytetrahydropyran-2-one disclosed and described in U.S. Pat. No. 4,900,754; ethyl E-(3R,5S)-7-[4'-fluoro-3,3',5-trimethyl(1,1')biphenyl-2-yl]-3,5-dihydroxy-6-heptenoate disclosed and described in U.S. Pat. No. 4,567,289; 3(R),5(S)-dihydroxy-7-[4-(4-fluorophenyl)-1-isopropyl-3-phenyl-1H-pyrazol-5-yl]hept-6(E)-enoic acid disclosed and described in U.S. Pat. No. 4,613,610; and (3R,5S)-BMY-21950 disclosed and described in U.S. Pat. No. 4,897,490 can be obtained using the present process. All of the aforementioned U.S. patents are herein incorporated by reference.

The process of the present invention in its first aspect is an improved, economical, and commercially feasible method for preparing a compound of Formula I. The process of the present invention in its first aspect is outlined in Scheme 1.

Scheme 1

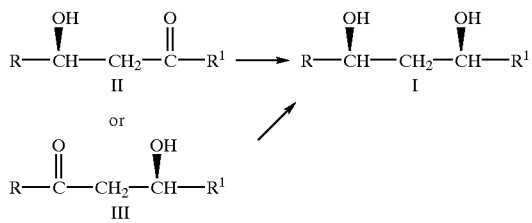

Thus, a compound of Formula II wherein R is alkyl,

NC—$CH_2$—,

PG—O—$CH_2$— wherein PG is a protecting group,

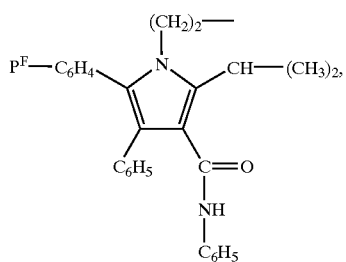

-continued

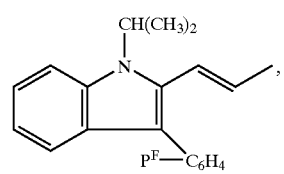

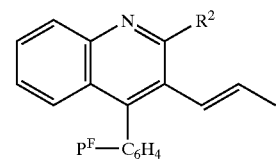

wherein $R^2$ is $(H_3C)_2CH$ or cyclopropyl,

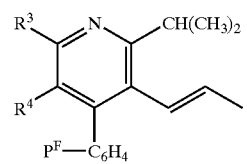

wherein $R^3$ is $C_6H_5$, $(H_3C)_2$—N— or $(H_3C)_2CH$— and $R^4$ is hydrogen, $H_3C$—O—$CH_2$—, $H_3C$—$CH_2$—$C(CH_3)_2$—$CO_2CH_2$—, or $H_3C$—$O_2C$—$CH_2$—$CH(OH)$—$CH_2$—

$CH(OH)$—$CH$=$CH$—,

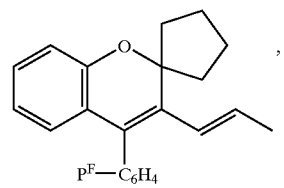

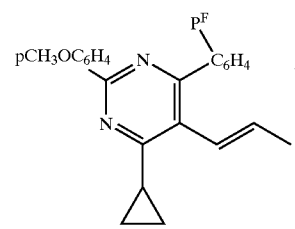

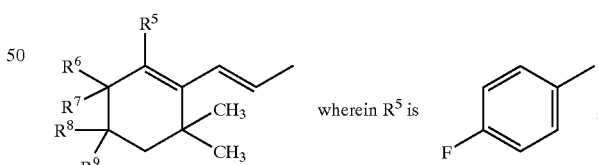

wherein $R^5$ is

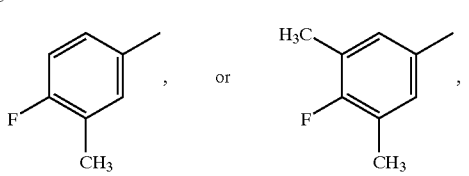

$R^6$ is hydrogen or $CH_3$, $R^7$ is hydrogen or $CH_3$, $R^8$ is hydrogen, OH, $CH_3$, or $H_5C_6$—NHCO—O—, and $R^9$ is hydrogen or $CH_3$, -continued

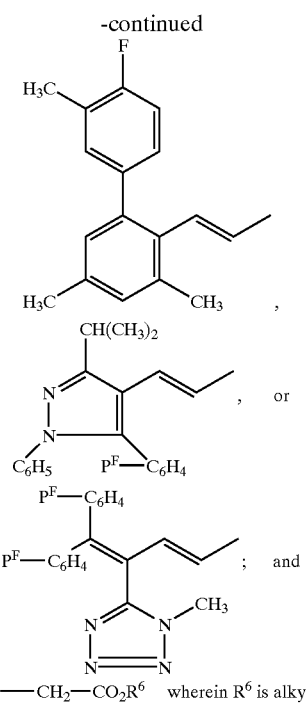

R¹ is alkyl, or —CH₂—CO₂R⁶ wherein R⁶ is alkyl;

or a compound of Formula III wherein R and R¹ are as defined above is treated with about 0.1 to about 2.0 molecular equivalents of a trialkylborane such as, for example, triethylborane, tripropylborane, tri n-butylborane, tri sec-butylborane and the like or a dialkylalkoxyborane such as, for example, dimethylmethoxyborane, dimethylethoxyborane, dimethylisopropoxyborane, diethylmethoxyborane, diethylethoxyborane, diethylisopropoxyborane, diisopropylmethoxyborane, diisopropylethoxyborane, diisopropylisopropoxyborane, and the like or a mixture of a trialkylborane and a dialkylalkoxyborane as described previously, followed by the stereoselective reduction with about 1 molecular equivalent of an alkali metal hydride such as, for example, sodium borohydride, zinc borohydride, lithium borohydride, lithium aluminum hydride, and the like; in a solvent such as a hydrocarbon, for example hexane, toluene, cyclohexane and the like; an alkanol, for example methanol, ethanol, isopropanol and the like; or an ether, for example diethyl ether, tetrahydrofuran, 1,2-dimethoxyethane, triglyme (triethylene glycol dimethyl ether) and the like, or mixtures thereof at a temperature of about −110° C. to about −50° C. to afford after concentration by distillation a compound of Formula I. Additional compound of Formula II or III is subsequently treated with the distillate obtained by vacuum distillation from the first run followed by stereoselective reduction carried out as described above to afford a second batch of a compound of Formula I. Thus, recovered quantities of the alkylborane species can be used to convert additional quantities of a compound of Formula II or III to a compound of Formula I. This procedure using recovered alkylborane species can be repeated as desired to obtain additional quantities of a compound of Formula I.

Preferably, the reaction is carried out with about 1.2 to 0.8 molecular equivalents of triethylborane or diethylmethoxyborane or a mixture of a trialkylborane and a dialkylalkoxyborane as described previously in a solvent, preferably a mixture of tetrahydrofuran and methanol, at a ratio of about 8 volumes of tetrahydrofuran to one volume of methanol. This is followed by the addition of about one molecular equivalent of sodium borohydride at about −110° C. to about −50° C., preferably at −80° C., followed by stirring for about 30 minutes to about 3 hours. Under these preferred conditions, greater than 90% of a compound of Formula I is produced in the desired stereochemical conformation.

Preferably, the present process is used to prepare [R-(R*,R*)]-1,1-dimethylethyl 6-cyano-3,5-dihydroxyhexanoate which is used as an intermediate to prepare atorvastatin. Compounds of Formula II or III are either known or capable of being prepared by methods known in the art.

The process of the present invention in its second aspect is an improved, economical, and commercially feasible method for preparing a compound of Formula I as previously outlined in Scheme 1.

In this aspect of the invention, applicants have found that a combination of a trialkylborane and a dialkylalkoxyborane surprisingly and unexpectedly is synergistic in selectively affording the desired cis-1,3-diol over the undesired trans-1,3-diol compared to the use of either a trialkylborane or a dialkylalkoxyborane alone. The synergistic combination comprises about 1% to 99% by weight of a trialkylborane and about 99% to 1% by weight of a dialkylalkoxyborane; preferably, a combination of about 90% by weight of a trialkylborane and 10% by weight of a dialkylalkoxyborane. This synergistic combination is of particular advantage since it does not require a stir time of the alkylborane species with the hydroxyketone at ambient temperature before reduction. The conditions and solvents for carrying out the reaction with a synergistic combination of a trialkylborane and a dialkylborane are as previously described above.

Thus, for example, in the preparation of [R-(R*,R*)]1,1-dimethylethyl 6-cyano-3,5-dihydroxyhexanoate when no pre-stir is used, triethylborane affords a 5 to 10:1 (cis:trans) mixture. When diethylmethoxyborane is used in place of triethylborane, a 5 to 10:1 (cis:trans) mixture is obtained. When a combination of 10% by weight of diethylmethoxyborane and 90% by weight of triethylborane is used, typically a greater than 30:1 (cis:trans) mixture is obtained. This synergistic effect of combining a dialkylalkoxyborane and a trialkylborane could not have been predicted based on the use of either reagent alone or literature precedent.

The following examples are illustrative to show the present processes and to show the usefulness in the preparation of (4R-Cis) 1,1-dimethylethyl-6-cyanomethyl-2,2-dimethyl-1,3-dioxane-4-acetate which is an intermediate prepared from a 1,3-diol of the present process that can be converted to atorvastatin ([R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, calcium salt (2:1)) (crystalline Form I) which is useful as a hypolipidemic and hypocholesterolemic agent.

EXAMPLE 1

(4R-Cis) 1,1-Dimethylethyl-6-cyanomethyl-2,2-dimethyl-1,3-dioxane-4-acetate

Step (1): Preparation of 5R 1,1-Dimethylethyl 6-cyano-5-hydroxy-3-oxohexanoate

To a vessel containing 265 kg of 16.8% n-butyllithium is added a mixture of 80 kg of diisopropylamine in 80 L of tetrahydrofuran maintaining the temperature at less than 20° C. The solution is cooled to −55° C., and 85 kg of tert-butyl acetate is added maintaining the temperature at −50°±5° C. A solution of 25 kg of R 4-cyano-3-hydroxybutanoic acid ethyl ester in 55 L of tetrahydrofuran is then added, and the temperature is allowed to warm to −20° C. for at least 20 minutes. The solution is then quenched by transferring to aqueous hydrochloric acid. The organic layer is separated and the aqueous layer re-extracted with ethyl acetate. The combined organic layers are concentrated by vacuum distillation to afford crude 5R 1,1-dimethylethyl 6-cyano-5-hydroxy-3-oxohexanoate.

Step (2): Preparation of [R-(R*,R*)]-1,1-Dimethylethyl 6-cyano-3,5-dihydroxyhexanoate Method A: Using Triethylborane Step (a):

Crude 5R 1,1-dimethylethyl 6-cyano-5-hydroxy-3-oxohexanoate (about 150 moles) from Step (1) is dissolved in 325 L of tetrahydrofuran containing about 20 kg of triethylborane, stirred for about 2 hours at room temperature, cooled to −75° C.±20° C. and diluted with 25 L of methanol and 8 kg of acetic acid. Sodium borohydride (8 kg) as a solution in methanol and aqueous sodium hydroxide is added slowly. After the addition, the reaction mixture is warmed to 0° C.±25° C. The reaction mixture is optionally quenched by the addition of 3 kg of acetic acid and 10 L of methanol and concentrated by vacuum distillation, saving the distillate. The residue is dissolved in methanol and acetic acid, optionally diluted with water, and concentrated by vacuum distillation, keeping this distillate separate from the first one. The residue is dissolved in methanol and concentrated by vacuum distillation. The residue is dissolved in a mixture of water and ethyl acetate, and the aqueous layer separated. The organic layer is concentrated by vacuum distillation. The residue is dissolved in methanol and acetic acid and concentrated by vacuum distillation. The residue is dissolved in ethyl acetate and concentrated by vacuum distillation affording crude [R-(R*,R*)]-1,1-dimethylethyl 6-cyano-3,5-dihydroxyhexanoate.

The cis:trans ratio was about 30:1 as measured after conversion to (4R cis and trans)1,1-dimethylethyl 6-cyanomethyl-2,2-dimethyl-1,3-dioxane-4-acetate according to the procedure described herein in Step 3.

Step (b): Reusing Recovered Triethylborane

Crude 5R 1,1-dimethylethyl 6-cyano-5-hydroxy-3-oxohexanoate (about 150 moles) from Step (1) is dissolved in the first distillate from Step (a) along with 50 L of tetrahydrofuran, cooled to −75° C.±20° C., and optionally diluted with 25 L of methanol, and 10 kg of acetic acid. Sodium borohydride (8 kg) as a solution in methanol and aqueous sodium hydroxide is added slowly. After the addition, the reaction mixture is warmed to 0° C.±25° C. The reaction mixture is quenched by the addition of 10 kg of acetic acid and 20 L of methanol and concentrated by vacuum distillation. The residue is dissolved in methanol and acetic acid, optionally diluted with water, and concentrated by vacuum distillation. The residue is dissolved in methanol and concentrated by vacuum distillation. The residue is dissolved in a mixture of water and ethyl acetate, and the aqueous layer separated. The organic layer is concentrated by vacuum distillation. The residue is dissolved in methanol and acetic acid and concentrated by vacuum distillation. The residue is dissolved in ethyl acetate and concentrated by vacuum distillation affording crude [R-(R*,R*)]-1,1-dimethylethyl 6-cyano-3,5-dihydroxyhexanoate.

The cis:trans ratio was about 40:1 as measured after conversion to (4R cis and trans) 1,1-dimethylethyl 6-cyanomethyl-2,2-dimethyl-1,3-dioxane-4-acetate according to the procedure described herein in Step 3.

Method B: Using Triethylborane

Step (a):

Crude 5R 1,1-dimethylethyl 6-cyano-5-hydroxy-3-oxohexanoate (about 130 mmoles) from Step (1) is dissolved in 100 mL 1 M triethylborane in THF and 65 mL tetrahydrofuran, stirred for about 2 hours at room temperature, then cooled to −75° C.±20° C., and diluted with 25 mL methanol. Sodium borohydride (6 g) as a solution in triglyme (75 mL) is added slowly. After the addition, the reaction mixture is warmed to 20° C. to 25° C. The reaction mixture is quenched by the addition of 20 mL methanol and 8 g acetic acid and concentrated by vacuum distillation—saving the distillate. The residue is diluted with 100 mL water and 200 mL ethyl acetate, agitated, and the phases separated. The organic layer is concentrated by vacuum distillation—keeping this distillate separate from the first one. The residue is dissolved in 200 mL methanol and 10 mL acetic acid and concentrated by vacuum distillation. The residue is dissolved in 200 mL methanol and concentrated by vacuum distillation. The residue is dissolved in 200 mL methanol and concentrated by vacuum distillation. The residue is dissolved in ethyl acetate and concentrated by vacuum distillation resulting in crude [R-(R*,R*)]-1,1-dimethylethyl 6-cyano-3,5-dihydroxyhexanoate.

The cis:trans ratio was about 20:1 as measured after conversion to (4R cis and trans) 1,1-dimethylethyl 6-cyanomethyl-2,2-dimethyl-1,3-dioxane-4-acetate according to the procedure described herein in Step 3.

Step (b): Reusing Recovered Triethylborane

Crude 5R1,1-dimethylethyl 6-cyano-5-hydroxy-3-oxohexanoate (about 130 mmoles) from Step (1) is dissolved in the first distillate from the above Step (a) mixture and cooled to −75° C.±20° C. Sodium borohydride (6 g) as a solution in 75 mL triglyme is added slowly. After the addition, the reaction mixture is warmed to 25° C. The reaction mixture is quenched by the addition of 8 g acetic acid (and optionally 20 mL methanol) and concentrated by vacuum distillation—saving the distillate. The residue is dissolved in a mixture of water (100 mL) and ethyl acetate (200 mL), the layers separated, and the organic layer is concentrated by vacuum distillation. The residue is dissolved with 200 mL methanol and 10 mL acetic acid and concentrated by vacuum distillation. The residue is dissolved with 200 mL methanol and concentrated by vacuum distillation. The residue is dissolved with 200 mL methanol and concentrated by vacuum distillation. The residue is dissolved in ethyl acetate and concentrated by vacuum distillation resulting in crude [R-(R*,R*)]-1,1-dimethylethyl 6-cyano-3,5-dihydroxyhexanoate.

The cis:trans ratio was about 30:1 as measured after conversion to (4R cis and trans) 1,1-dimethylethyl 6-cyanomethyl-2,2-dimethyl-1,3-dioxane-4-acetate according to the procedure described herein in Step 3.

Step (c): Reusing Recovered Triethylborane

Following the procedure of the previous Step (b) crude 5R-1,1-dimethylethyl 6-cyano-5-hydroxy-3-oxohexanoate (about 130 mmoles) from Step (1) is reacted with recovered triethylborane from Step (b) to afford crude [R-(R*,R*)]-1,1-dimethylethyl 6-cyano-3,5-dihydroxyhexanoate.

The cis:trans ratio was about 30:1 as measured after conversion to (4R cis and trans) 1,1-dimethylethyl 6-cyanomethyl-2,2-dimethyl-1,3-dioxane-4-acetate according to the procedure described herein in Step 3.

Method C: Using Diethylmethoxyborane

Step (a):

Crude 5R 1,1-dimethylethyl 6-cyano-5-hydroxy-3-oxohexanoate (about 150 mmoles) is dissolved by adding 22 mL diethylmethoxyborane and 200 mL tetrahydrofuran. The solution is stirred for about 2 hours at room temperature, then cooled to −70° C. to −75° C., and further diluted with 25 mL methanol. Sodium borohydride (6 g) as a solution in triglyme (75 mL) is added slowly at between −65° C. to −75° C. After the addition, the reaction mixture is warmed to 15° C. to 25° C., quenched by the addition of acetic acid and concentrated by vacuum distillation—keeping this distillate. The residue is diluted with methanol and concentrated by vacuum distillation—keeping this distillate and all subsequent ones separate from the first one. The residue is dissolved in a mixture of water and ethyl acetate, the layers separated, and the organic layer is concentrated by vacuum distillation. The residue is dissolved in methanol and acetic acid and concentrated by vacuum distillation. The residue is dissolved in ethyl acetate and concentrated by vacuum distillation resulting in crude [R(R*,R*)]-1,1-dimethylethyl 6-cyano-3,5-dihydroxyhexanoate.

The cis:trans ratio was about 35:1 as measured after conversion to (4R cis and trans) 1,1-dimethylethyl 6-cyanomethyl-2,2-dimethyl-1,3-dioxane-4-acetate according to the procedure described herein in Step 3.

Step (b): Reusing Recovered Diethylmethoxyborane

Crude 5R 1,1-dimethylethyl 6-cyano-5-hydroxy-3-oxohexanoate (about 150 mmoles) is dissolved in the first distillate from the above mixture, allowed to stir at room temperature for about 2 hours, and cooled to about −70° C. Sodium borohydride (6 g) as a solution in 75 mL triglyme is added slowly at between −65° C. to −75° C. After the addition, the reaction mixture is warmed to 15° C. to 25° C., quenched by the addition of acetic acid and concentrated by vacuum distillation. The residue is diluted with methanol and concentrated by vacuum distillation. The residue is dissolved in a mixture of water and ethyl acetate, the layers separated, and the organic layer is concentrated by vacuum distillation. The residue is dissolved with methanol and acetic acid and concentrated by vacuum distillation. The residue is dissolved in ethyl acetate and concentrated by vacuum distillation resulting in crude [R(R*,R*)]-1,1-dimethylethyl 6-cyano-3,5-dihydroxyhexanoate.

The cis:trans ratio was about 25:1 as measured after conversion to (4R cis and trans) 1,1-dimethylethyl 6-cyanomethyl-2,2-dimethyl-1,3-dioxane-4-acetate according to the procedure described herein in Step 3.

Method D: Using a Mixture of Diethylmethoxyborane and Triethylborane

Step (a):

Crude 5R 1,1-Dimethylethyl 6-cyano-5-hydroxy-3-oxohexanoate (about 150 mmoles) is dissolved in 170 mL tetrahydrofuran. The solution is cooled to −70° C. to 75° C., and further diluted with 115 mL of 14% triethylborane in tetrahydrofuran, 4 mL diethylmethoxyborane, 45 mL methanol, and 8 mL acetic acid. Sodium borohydride (7 g) as a solution in methanol (65 mL) containing 50% aqueous sodium hydroxide (3.2 g) is added slowly at between −70° C. to −75° C. After the addition, the reaction mixture is warmed to 15° C. to 25° C., quenched by the addition of acetic acid, and concentrated by vacuum distillation—keeping the distillate. The residue is diluted with methanol and concentrated by vacuum distillation—keeping this distillate and all subsequent ones separate from the first one. The residue is dissolved in a mixture of water and ethyl acetate, the layers separated, and the organic layer is concentrated by vacuum distillation. The residue is dissolved in methanol and acetic acid and concentrated by vacuum distillation. The residue is dissolved in ethyl acetate and concentrated by vacuum distillation resulting in crude [R-(R*,R*)-1,1-dimethylethyl 6-cyano-3,5-dihydroxyhexanoate.

The cis:trans ratio was >50:1 as measured after conversion to (4R cis and trans) 1,1-dimethylethyl 6-cyanomethyl-2,2-dimethyl-1,3-dioxane-4-acetate according to the procedure described herein in Step 3.

Step (b): Reusing Recovered Triethylborane and Diethylmethoxyborane Mixture

Following the procedure in Step (2)(b) as described in Method A affords [R-(R*,R*)-1,1-dimethylethyl 6-cyano-3,5-dihydroxyhexanoate.

Step (3): Preparation of (4R cis) 1,1-Dimethylethyl 6-cyanomethyl-2,2-dimethyl-1,3-dioxane-4-acetate Crude [R-(R*,R*)]-1,1-dimethylethyl 6-cyano-3,5-dihydroxyhexanoate (about 150 moles) from Step (2) is diluted with 100 kg of 2,2-dimethoxypropane and acidified with about 1 L of methanesulfonic acid. The reaction is quenched by the addition of aqueous sodium bicarbonate solution and concentrated by vacuum distillation. The residue is diluted with 150 L of hexane, and the layers separated. The organic layer is washed with aqueous sodium bicarbonate solution and cooled to 0° C.±10° C. to crystallize. The product is collected by filtration and washed with cooled hexane, then dried affording 28.5 kg of (4R cis) 1,1-dimethylethyl 6-cyanomethyl-2,2-dimethyl-1,3-dioxane-4-acetate.

EXAMPLE 2

[R-(R*,R*)]-2-(4-Fluorophenyl)-β,δ-dihydroxy-5-(1-methylethyl)-3-phenyl-4-[(phenylamino)carbonyl]-1H-pyrrole-1-heptanoic acid, calcium salt (2:1) (crystalline Form I)

Step (1): Preparation of (4R-cis)-1,1-dimethylethyl 6-(2-aminoethyl)-2,2-dimethyl-1,3-dioxane-4-acetate (4R-cis)1,1-Dimethylethyl 6-cyanomethyl-2,2-dimethyl-1,3-dioxane-4-acetate (Example 1) is converted to the title compound using the methodology disclosed at Column 49, Lines 16–43 of U.S. Pat. No. 5,003,080.

Step (2): Preparation of (4R-cis)-1,1-Dimethylethyl 6-[2[2-(fluorophenyl)-5-(-(1-methylethyl)-3-phenyl-4-[(phenylamino)carbonyl]-1H-pyrrol-1-yl]ethyl]-2,2-dimethyl-1,3-dioxane-4-acetate (4R-cis)-1,1-Dimethylethyl 6-(2-aminoethyl)-2,2-dimethyl-1,3-dioxane-4-acetate is converted to the title compound using the methodology disclosed at Column 49, Lines 43–60 of the U.S. Pat. No. 5,003,080.

Step (3): Preparation of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (4R-cis)-1,1-Dimethyl 6-(2-aminoethyl)-2,2-dimethyl-1,3-dioxane-4-acetate is converted to the title compound using the methodology disclosed at Column 50, Lines 4–30 of U.S. Pat. No. 5,003,080.

Step (4): Preparation of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid, calcium salt (2:1) (crystalline Form I)

(2R-trans)-5-(4-Fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is converted to the title compound using the methodology disclosed in copending U.S. patent application Ser. No. 08/945,812.

What is claimed is:

1. A process for the preparation of a compound of Formula I

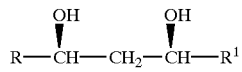

wherein R is,

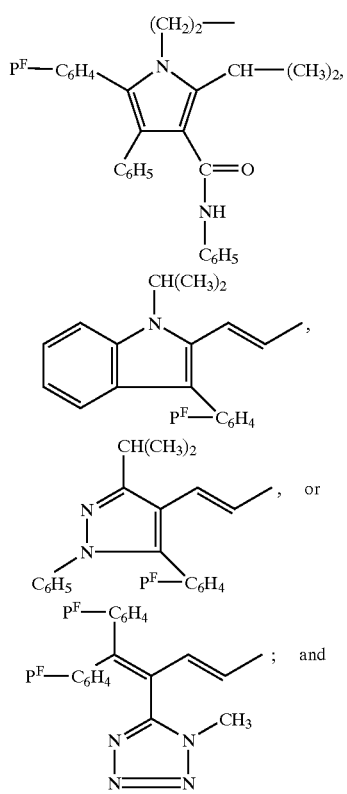

$R^1$ is alkyl, or —$CH_2$—$CO_2R^6$ wherein $R^6$ is alkyl;

which comprises:

Step (a) treating a compound of Formula II

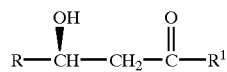

or a compound of Formula III

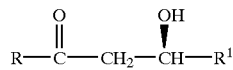

wherein R and $R^1$ are as defined above with a trialkylborane or dialkylalkoxyborane or a mixture of a trialkylborane and a dialkylalkoxyborane in a solvent;

Step (b) adding an alkali metal hydride at about −110° C. to about −50° C.;

Step (c) concentrating the reaction by distillation to afford a compound of Formula I and a distillate containing alkylborane species; and Step (d) treating additional compound of Formula II or III with the distillate from Step (c) containing recovered alkylborane species, and repeating Steps (b) and (c) as desired to afford additional compound of Formula I.

2. The process according to claim 1 wherein the trialkylborane in Step (a) is triethylborane.

3. The process according to claim 1 where in the dialkylalkoxyborane in Step (a) is diethylmethoxyborane.

4. The process according to claim 1 wherein the solvent in Step (a) is selected from the group consisting of: tetrahydrofuran; methanol; and a mixture of tetrahydrofuran and methanol.

5. The process according to claim 1 wherein the distillation in Step (c) is a vacuum distillation.

6. The process according to claim 1 wherein PG is benzyl.

7. The process according to claim 1 wherein the alkali metal hydride is sodium borohydride.

8. The process according to claim 1 for the preparation of [R-(R*,R*)]-1,1-dimethylethyl 6-cyano-3,5-dihydroxyhexanoate.

9. The process according to claim 1 for the preparation of the compound of Formula Ia

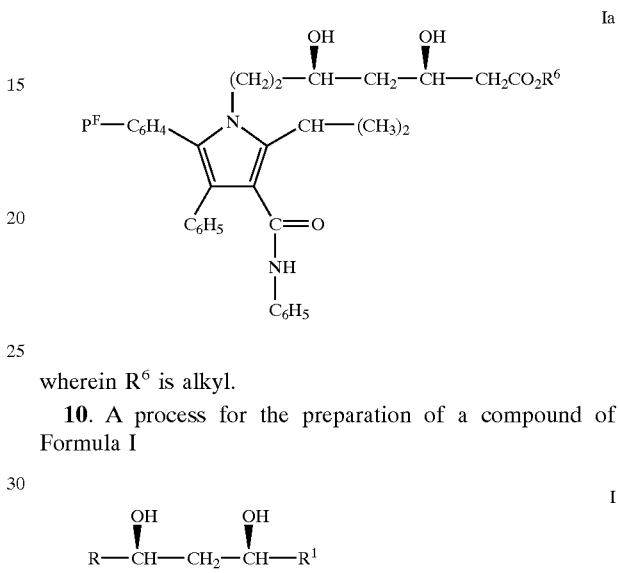

wherein $R^6$ is alkyl.

10. A process for the preparation of a compound of Formula I $$R—\overset{OH}{\underset{|}{CH}}—CH_2—\overset{OH}{\underset{|}{CH}}—R^1$$

I wherein R is,

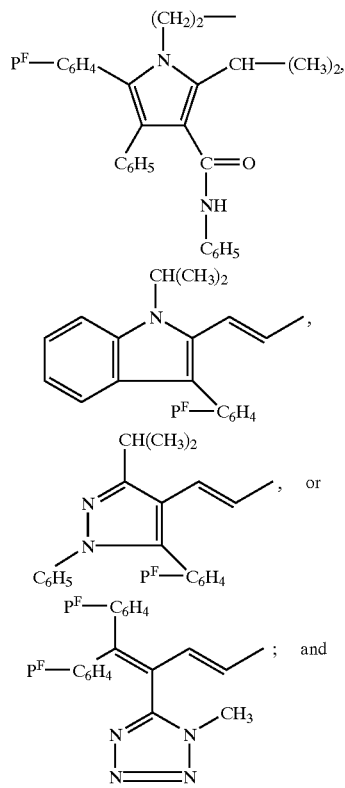

-continued $R^1$ is alkyl, or —$CH_2$—$CO_2R^6$ wherein $R^6$ is alkyl;

which comprises:

Step (a) treating a compound of Formula II

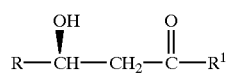

II or a compound of Formula III

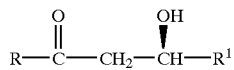

III wherein R and $R^1$ are as defined above with a synergistic combination of a trialkylborane and a dialkylalkoxyborane in a solvent; and Step (b) adding an alkali metal hydride at about −110° C. to about −50° C. to afford a compound of Formula I.

11. The process according to claim 10 wherein the trialkylborane in Step (a) is triethylborane.

12. The process according to claim 10 wherein the dialkylalkoxyborane in Step (a) is diethylmethoxyborane.

13. The process according to claim 10 wherein the solvent Step (a) is selected from the group consisting of: tetrahydrofuran; methanol; and a mixture of tetrahydrofuran and methanol.

14. The process according to claim 10 wherein the alkali metal hydride is sodium borohydride.

15. The process according to claim 10 for the preparation of [R-(R*,R*)]-1,1-dimethylethyl 6-cyano-3,5-dihydroxyhexanoate.

16. The process according to claim 10 for the preparation of the compound of Formula Ia

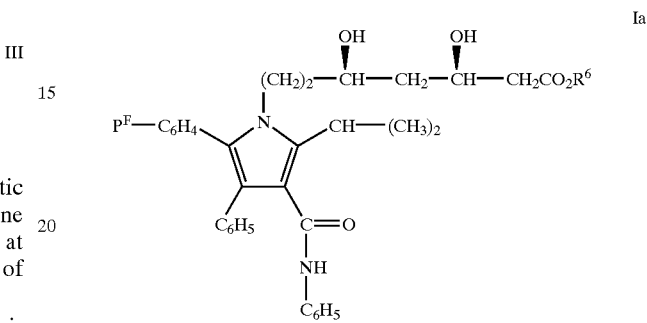

wherein $R^6$ is alkyl.

* * * * *